United States Patent [19]

Poler

[11] Patent Number: 4,540,417

[45] Date of Patent: Sep. 10, 1985

[54] EYE-MEDICATING HAPTIC

[76] Inventor: Stanley Poler, 78 E. Second St., New York, N.Y. 10003

[21] Appl. No.: 490,958

[22] Filed: May 2, 1983

[51] Int. Cl.³ .............................................. A61M 7/00
[52] U.S. Cl. .................................. 604/895; 604/294; 623/5
[58] Field of Search ....................... 604/895, 294, 892; 3/13 A; 351/160 R, 160 H

[56] References Cited

U.S. PATENT DOCUMENTS

| | | | |
|---|---|---|---|
| 3,786,812 | 1/1974 | Neefe | 604/895 |
| 4,056,496 | 11/1977 | Mancini et al. | 604/895 X |
| 4,057,619 | 11/1977 | Higuchi et al. | 604/895 X |

FOREIGN PATENT DOCUMENTS

| | | | |
|---|---|---|---|
| 1003914 | 3/1957 | Fed. Rep. of Germany | 604/895 |
| 2071352 | 9/1981 | United Kingdom | 3/13 A |

*Primary Examiner*—Stephen C. Pellegrino
*Attorney, Agent, or Firm*—Hopgood, Calimafde, Kalil, Blaustein & Judlowe

[57] ABSTRACT

The invention contemplates eye-medicating haptic constructions which are fenestrated and provide the vehicle for eye medication. The haptic structure is initially flat but axially flexible as to be self-adapting to the surface of the cornea and to be self-retaining of its position, via moisture at the surface of the cornea. Medication carried by the haptic is made available to the surface of the cornea by mild pumping action of haptic structure on corneal fluid, the medication being drawn from storage in the haptic, by the wash of liquid involved in the pump action.

23 Claims, 10 Drawing Figures

EYE-MEDICATING HAPTIC

BACKGROUND OF THE INVENTION

The invention relates to structures which are self-adherent to the surface of the cornea and which are the vehicle of one or more medicaments for the eye.

In my U.S. Pat. No. 4,377,329, contact-lens configurations are described wherein the lens is a relatively small central component, and a surrounding haptic is a second component. The haptic is substantially fenestrated and is so thin and flexible that, although normally flat, being formed from flat sheet material, it is self-adapting to the curvature of the cornea, and it remains removably adhered to the cornea via normal moisture on the surface of the cornea. The entire structure is so thin as to cause no discomfort, in spite of normal eyelid action, and the eyelid action operates upon the fluid suspension of the haptic in such manner as to assure circulation of fluid in the moist region between all parts of the haptic and the cornea.

In a recent article entitled, "Polymers Release Drugs Continuously", *High Technology*, January 1983, pages 28 to 31, new drug systems are described for delivery of medical dosages at desired rates for extended periods of time. In particular, bio-compatible polymers are described wherein particular drugs are built into the polymer for diffusion, as from a capsule, in the course of time. Among the products described is a relatively expensive one for use in the eye, wherein a plastic disk sits continuously on the eyeball behind the lower eyelid, releasing pilocarpine for glaucoma therapy. The disk is said to function for a week, producing fewer side effects than the administration of pilocarpine with eyedrops. Such disks are relatively bulky and awkward to insert and remove, and they must be preshaped for conformance to the surface of the eyeball.

BRIEF STATEMENT OF THE INVENTION

It is an object of the invention to produce an improved eye-medicating device of the character indicated.

It is a specific object to meet the above object with structure which is self-adapting and removably self-adherent to the surface of the cornea and which does not optically interfere with normal operation of the eye.

A general object is to achieve these objects with structure which is inherently simple, safe and inexpensive.

The invention achieves the above objects with haptics as in said patent, wherein initially flat and thin fenestrated structures are so compliant as to be removably self-adapting to the curvature of the cornea, adhering solely via moisture on the cornea. The haptics are annular, with a central opening so as to not interfere with normal vision, and they are of selected materials, such as hydrophilic materials having an ability to store medication, for slow release in the presence of natural moisture of the eye, and aided by normal blinking eyelid action.

DETAILED DESCRIPTION

The invention will be described in detail for several embodiments, in conjunction with the accompanying drawings, in which:

FIGS. 1 to 5 illustrate a variety of annular haptic structures which feature substantial fenestration of initially flat thin plastic sheet material, having the ability to not only self-adapt and removably adhere to the surface of the cornea, but also to retain and slowly release medication when thus adhered.

Figure 1:
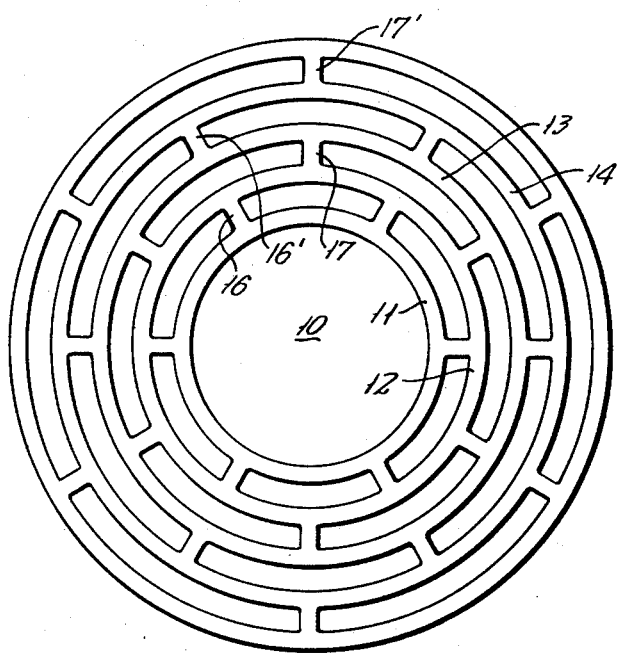
FIG. 1 is a plan view of an eye-medicating haptic of the invention.

The embodiment of FIG. 1 features circumferential continuity, providing a succession of radially spaced concentric rings 11–12–13–14–15, about a central opening 10. These concentric rings are integrally connected by first sets of angularly spaced radial connections 16–16' between rings 11–12 and 13–14, and by further sets of such connectors 17–17' between rings 12–13 and 14–15; the sets 16–16' and 17–17' are in angularly staggered interlace. The diameter of opening is desirably 6 to 8 mm, for general conformance with iris diameter and therefore so as not to interfere with normal vision, and the outer diameter of outer ring 15 may be 12 to 14 mm. Except for opening 10 in place of a lens, the planiform of the haptic of FIG. 1 will be recognized from my copending application, Ser. No. 467,436, filed Feb. 17, 1983, to which reference is made as to self-adaptation and other features in application to the surface curvature and moisture of the cornea.

Figure 2:
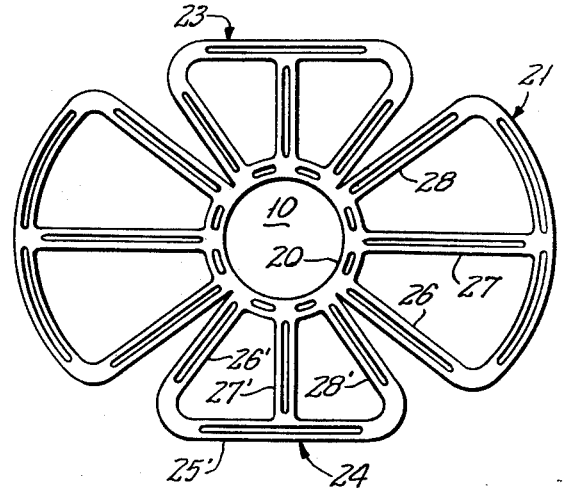
FIGS. 2 to 5 are views similar to FIG. 1, for each of a plurality of different embodiments.

The haptic configuration of FIG. 2 will be recognized from my said U.S. Pat. No. 4,377,329, again except for provision of a central circular opening 10 in place of a lens. In the structure of FIG. 2, an inner ring 20 is circumferentially continuous, and opposed pairs of fenestrated feet 21–22 and 23–24 extend radially. Each foot comprises an outer arcuate or transverse tie, as at 25 (25'), integrally connecting three radial legs 26–27–28 (26'–27'–28'), and elongate slots in all component members 20 to 28 of the haptic provide passages for fluid access (e.g., fluid pumping) or medication storage, in addition to enhancing the inherently flexible and contour-adapting nature of the construction.

Figure 3:
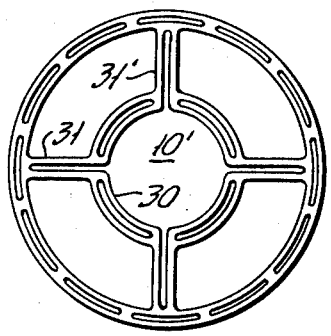

FIG. 3 illustrates a modified haptic in which the central opening 10' is not circumferentially continuous but, rather, it is an angularly spaced succession of arcuate inner ties 30 integrally connected by spaced legs 31–31' to a circumferentially continuous outer ring 32; thus, in FIG. 3, angularly spaced compliant foot formations extend radially inward from the circumferentially continuous outer ring 32. Narrow slots in integrally connected members of the structure serve fluid and/or medication-storage functions mentioned in connection with FIG. 2.

Figure 4:
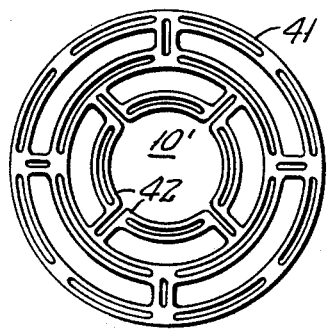

In the embodiment of FIG. 4, a circumferentially continuous circular ring member 40 is intermediate (a) the outer arcuate limits of angularly spaced radially outward foot formations 41 and (b) the inner arcuate limits of angularly spaced radially inward foot formations 42, within which the central opening 10' is again not circumferentially continuous. This design will be seen to provide a great number of slotted members for the fluid and/or medication-storage functions indicated.

Figure 5:
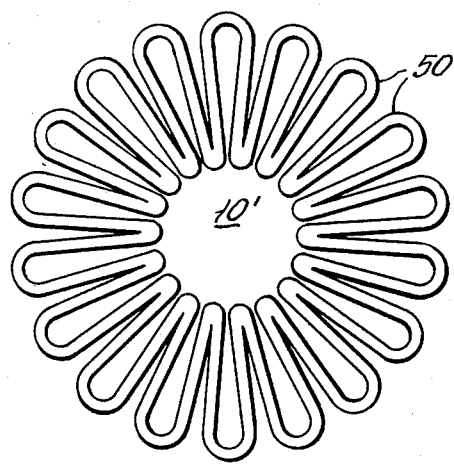

In the embodiment of FIG. 5, there is no circumferentially continuous ring, but the equivalent of a substantially fenestrated structure is provided by a radially undulating course of a single continuous strand, defining plural closing angularly spaced lobes 50 and leaving a central opening 10' which is not continuously circular.

All the structures thus far described will be understood to be normally flat, each being formed from a single sheet of thin plastic material inert to body fluids. The formative process may be a selected one of photo-etch, ion erosion, and the like procedures which I have described in U.S. Pat. No. 4,080,709, being adapted to production in multiple upon a single sheet of suitable plastic. Materials presently considered suitable in such sheets illustratively include cellulose acetate butyrate, cellulose acetate propionate, silicones and silicone acrylates, polymethypentene, polytrichloroethylene, polyvinylidenefluoride, and H.E.M.A., the latter four being hydrophilic and therefore suitable for soaked up storage of medication, such as boric-acid solution commonly used for relief of eye strain or a "burning" sensation. Sheet gelatin is another candidate for formation into haptics by the indicated procedures, and sheet gelatin has the advantage that it may initially be compounded with desired medication and that it may dissolve slowly as it makes it compounded medication available; ultimately, therefore, haptics of sheet gelatin will completely dissolve, and throughout the process of dissolving they will continuously make any medication available via surface moisture of the cornea.

Figure 6:
FIG. 6 is an enlarged fragmentary sectional view to illustrate a laminated construction for any of the forms of FIGS. 1 to 5.

FIG. 6 illustrates that any one of the above described types of haptic may in fact be the product of bonding plural (e.g., two) very thin plies 60–61 to each other. In the form shown, one (61) of these plies is pocked with foraminations, defining spaced pockets 62 which are receptors for the storage and slow releasability of medication, primarily directed via surface moisture on the cornea, or on the inner surface of the upper eyelid, depending upon whether the pockets 62 face inwardly or outwardly when applied to the corneal surface.

Figure 7:
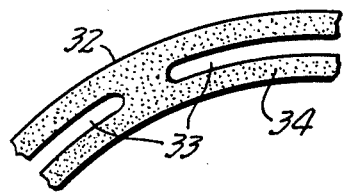
FIG. 7 is an enlarged fragmentary plan view to illustrate another construction for any of the forms of FIGS. 1 to 5.

FIG. 7 illustrates a fragment of slotted haptic structure, e.g., ring 32 of FIG. 3, wherein the full thickness of a single ply is foraminated for the indicated purposes. As seen in FIG. 7, the foraminations are in great number and much smaller than the size of slots 33 of ring 32, the foraminations being shown in FIG. 7 by stippling 34.

Figure 8:
FIGS. 8 to 10 are views similar to FIG. 6, to illustrate more embodiments.

FIG. 8 illustrates that the equivalent of the FIG. 6 structure may be achieved in a single ply 70 which is only partially etched or eroded from one side, to define receptor pockets 71 for storage and slow releasability of medication.

Figure 9:

FIG. 9 illustrates that a structure as in FIG. 6 may be modified to the extent that the plies 60'-61' may be laminated to each other via a layer 73 of medication. Foraminations 62' in the covering layer 61' provide passages through which moisture of the eye can weep for controlled pick-up and external release of medication. If the layer 61' is of plastic material, then the foraminations 62' will remain with constant open area as the medication is gradually dissolved and released, ultimately delaminating layers 60'-61' from each other, at which point the exhausted layers 60'-60' may be discarded. On the other hand, if the layer 61' is a dissolvable membrane, as of gelatin, then the foraminations 62' will enlarge in area in the course of the fluid flow which releases medication, thus progressing the access to stored medication 73 as the medication is consumed.

Figure 10:

In the arrangement of FIG. 10, an article as in FIG. 6, namely, a foraminated ply 61 adhered to a base ply 60 and providing pockets 62 loaded with medication, may be caused to provide a slower rate of medication release, by applying a thin layer 75 over the loaded ply 61. Layer 75 is characterized by a dense pattern of pinholes (denoted by upright lines in FIG. 10), the pinholes being each in the order of 0,001-inch diameter and of very much smaller sectional area, e.g., 10 percent, of the area of each of the foraminations which define pockets 62 of the ply 61.

It will be understood that what has been said in connection with FIG. 10 applies equally to the situation wherein medication is loaded in the pockets 71 of the single-ply article of FIG. 8 and wherein a thin layer 75 characterized by a dense pattern of pinholes (as in FIG. 10) is applied as a covering ply to the pocked side of ply 70 of FIG. 8.

The described structures will be seen as illustrative vehicles for medication to serve via the surface moisture of the cornea. All described haptics are not only self-adapting to curvature of the cornea but are also self-adherent via the surface moisture. Still further, the nature of all described structures is to flex by slight local twisting when the eyelid blinks, giving rise to mild pumping action on the surface liquid and thereby aiding in release and distribution of stored medication. The sheet material may be soluble, as in the case of sheet gelatin; it may be a protein substance such as collagen; and it may be a deliquescent carrier of the medication. Still further, it may be merely "spongy" to a degree, whereby the user may remove the haptic after use, then soak it in medication (e.g., boric-acid or other medicating solution), for reapplication to the eye.

In all cases, the described structures do not interfere with normal optical functions of the eye. For example, for those requiring no optical correction for good vision, the eye will always see through the central opening 10 (10'); and for those having a contact lens, the haptic of any of the described forms may be easily applied over or beneath the user's existing contact lens, whatever its configuration.

It will be appreciated that among the indicated available sheet materials, there is some variation in strength, flexibility, and like properties, as a function of material thickness. Generally, however, it may be stated that thickness of the indicated haptics is in the order of 0.001 inch, and in the case of plied structure as in FIGS. 6, 9 and 10, the thickness of individual plies 60–61 is in the order of 0.0005 inch.

It will also be appreciated that timed release of medication may be either primarily a function of sectional area of pockets or foraminations, or it may be primarily a function of pocket depth, depending upon area/depth proportions and upon the nature of the medication and of the eye-surface moisture condition of the patient for whom the medication is prescribed or intended.

While the invention has been described in detail for preferred forms, it will be understood that modifications may be made without departing from the scope of the invention. For example, although the forms of FIGS. 1 and 2 have been described as having a continuous inner ring to define the circular opening 10, the inner formation at 10 may be clear plastic sheet through which normal vision may proceed; in such case, the only fenestrations of the entire device are those described for the annulus outside of the inner region 10, with which the sheet material at region 10 is integrally and continuously united. And, of course, such sheet material at 10 may be characterized by a few spaced openings of such small size and number as to provide no noticeable degradation of normal vision while also preventing corneal-fluid entrapment beneath the sheet region 10, as discussed at greater length for some of the embodiments disclosed in my copending patent application, Ser. No. 225,349, filed Jan. 15, 1981.

What is claimed is:

1. As an article of manufacture adapted for self-adherent removable mounting to the cornea of an eye, an eye-medicating haptic comprising an annular body of flexible sheet material having a central opening sized to span a fully dilated pupil, said body being (1) substantially fenestrated throughout the annular area thereof and (2) of such compliant action as to deform in continuous smooth conformance to the surface curvature of the cornea and to adhere thereto solely through contact with natural moisture of the surface of the cornea, the material of said haptic being characterized by a plurality of medicament pockets, whereby said body is adapted to carry medication releasable on contact with such moisture.

2. The article of claim 1, in which said sheet material is hydrophilic.

3. The article of claim 1, in which said sheet material contains medication impregnated therein.

4. The article of claim 1, in which medication is adhered to and within fenestrations of said annular body.

5. The article of claim 1, in which deliquescent medication is adhered to said annular body.

6. The article of claim 1, in which medication is adhered to both sides of said annular body.

7. The article of claim 1, in which medication is adhered to one side of said annular body, the other side having a surface texture which is visually different from the appearance of the medicated side.

8. The article of claim 1, in which said annular body comprises a peripherally continuous outer rim, with the fenestrations of said body encompassed by said rim.

9. The article of claim 1, in which said annular body comprises a peripherally continuous inner ring defining the central opening, with the fenestrations of said body radially outside said ring.

10. The article of claim 1, in which said annular body comprises a peripherally continuous ring region at radially outward offset from the central opening, with the fenestrations of said body radially within said ring and radially outward of said ring.

11. As an article of manufacture adapted for self-adherent removable mounting to the cornea of an eye, an eye-medicating haptic comprising an annular body of flexible sheet material having a central opening sized to span a fully dilated pupil, said body being (1) substantially fenestrated throughout the annular area thereof and (2) of such compliant action as to deform in continuous smooth conformance to the surface curvature of the cornea and to adhere thereto solely through contact with natural moisture of the surface of the cornea, said body carrying medication releasable on contact with such moisture, and said body comprising a continuous narrow strip of radial undulations as a function of circumferential progression around the central opening.

12. The article of claim 1 or claim 11, in which said material is soluble in moisture of the eye.

13. The article of claim 1 or claim 11, in which the sheet material is a protein substance.

14. The article of claim 1 or claim 11, in which the sheet material is gelatin.

15. The article of claim 1 or claim 11, in which said sheet material is in the thickness range of 0.0005 to 0.002 inch.

16. The article of claim 1 or claim 11, in which said material is a single sheet characterized by medication-retaining pockets open to one side and terminating short of the other side.

17. As an article of manufacture adapted for self-adherent removable mounting to the cornea of an eye, an eye-medicating haptic comprising an annular body of sheet material having a central opening sized to span a fully dilated pupil, said body being (1) substantially fenestrated throughout the annular area thereof and (2) of such compliant action as to deform in continuous smooth conformance to the surface curvature of the cornea and to adhere thereto solely through contact with natural moisture of the surface of the cornea, said sheet material comprising at least two thin laminated sheets, one of which is foraminous, whereby the foraminated side defines pockets to releasably retain medication.

18. The article of claim 17, in which the individual thickness of said laminated sheets is in the order of 0.0005 inch.

19. The article of claim 17, in which the fenestrated openings of said body are larger than the foraminations.

20. The article of claim 17, in which said sheet material further includes a third thin laminated sheet which is porous and which otherwise covers the otherwise unlaminated side of said foraminated sheet.

21. As an article of manufacture adapted for self-adherent removable mounting to the cornea of an eye, an eye-medicating generally circular patch of transparent flexible sheet material said patch being substantially fenestrated throughout an outer annular area thereof, said outer annular area being radially outside a central circular area substantially conforming to the diameter of a fully dilated pupil, and said patch being of such compliant action as to deform in continuous smooth contact with the surface curvature of the cornea and to adhere thereto solely through contact with natural moisture of the surface of the cornea said material being characterized by a distributed plurality of medicament pockets, whereby said patch is adapted to carry medication releasable on contact with such moisture.

22. The article of claim 21, in which the periphery of said annulus conforms generally to the periphery of a contact lens and in which the deformable compliant action is so gentle as not to impair the ability of the lens when fitted over said patch to adhere to the cornea via eye moisture over said patch.

23. As an article of manufacture adapted for self-adherent removable mounting to the cornea of an eye, an eye-medicating haptic comprising an annular body of flexible sheet material having a central opening sized to span a fully dilated pupil, said body being (1) substantially fenestrated throughout the annular area thereof and (2) of such compliant action as to deform in continuous smooth conformance to the surface curvature of the cornea and to adhere thereto solely through contact with natural moisture of the surface of the cornea, said body carrying medication releasable on contact with such moisture.

* * * * *